(12) United States Patent
Maubru

(10) Patent No.: US 7,056,346 B1
(45) Date of Patent: Jun. 6, 2006

(54) DIRECT DYE COMPOSITION FOR THE HAIR, COMPRISING A CROSSLINKED POLYMER CONTAINING ACRYLIC UNITS AND C10-C30 ALKYL ACRYLATE UNITS

(75) Inventor: Mireille Maubru, Chatou (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/663,942

(22) Filed: Sep. 18, 2000

Related U.S. Application Data

(63) Continuation-in-part of application No. 09/068,964, filed as application No. PCT/FR97/00885 on May 20, 1997, now Pat. No. 6,136,042.

(30) Foreign Application Priority Data

May 23, 1996 (FR) .................... 96 06430

(51) Int. Cl.
    *A61K 7/13*    (2006.01)

(52) U.S. Cl. ............... 8/405; 8/428; 8/437; 8/451; 8/454; 8/466; 8/509; 8/552; 8/558; 8/676; 534/683; 552/208

(58) Field of Classification Search .......... 8/411, 8/420, 558, 405, 428, 451, 437, 454, 466, 8/509, 552, 676; 430/260, 100; 526/238.23; 534/683; 552/208

See application file for complete search history.

(56) References Cited

U.S. PATENT DOCUMENTS

| | | | |
|---|---|---|---|
| 3,915,921 A | 10/1975 | Schlatzer et al. | 260/17.4 |
| 3,919,265 A | 11/1975 | Bugaut et al. | 260/396 |
| 3,929,404 A | 12/1975 | Kalopissis et al. | 8/10.1 |
| 3,930,865 A | 1/1976 | Faust et al. | 96/86 |
| 4,023,926 A | 5/1977 | Bugaut et al. | 8/10 |
| 4,046,786 A | 9/1977 | Kalopissis et al. | 8/10.1 |
| 4,084,052 A | 4/1978 | Bugaut et al. | 544/165 |
| 4,092,102 A * | 5/1978 | Halasz et al. | 8/11 |
| 4,093,806 A | 6/1978 | Kalopissis et al. | 544/165 |
| 4,112,155 A | 9/1978 | Carel et al. | 427/439 |
| 4,124,386 A * | 11/1978 | Yoshida et al. | 96/29 |
| 4,145,299 A | 3/1979 | Ford, Jr. et al. | 252/62.1 |
| 4,204,059 A | 5/1980 | Bugaut et al. | 544/166 |
| 4,213,960 A | 7/1980 | Grollier et al. | 424/47 |
| 4,260,749 A | 4/1981 | Bugaut et al. | 544/166 |
| 4,402,977 A | 9/1983 | Grollier et al. | 424/70 |
| 4,509,949 A | 4/1985 | Huang et al. | 586/558 |
| 5,030,443 A | 7/1991 | Varco et al. | 424/47 |
| 5,102,655 A * | 4/1992 | Yoshihara et al. | 424/70 |
| 5,685,882 A | 11/1997 | Samain et al. | 8/408 |
| 5,891,200 A * | 4/1999 | Lim et al. | 8/406 |
| 5,989,295 A | 11/1999 | De Le Mettrie et al. | 8/406 |

FOREIGN PATENT DOCUMENTS

| | | | |
|---|---|---|---|
| DE | 3 044 754 | | 6/1981 |
| DE | 3834142 | * | 4/1990 |
| DE | 9 413 897 | | 2/1996 |
| EP | 0 410393 A2 | | 1/1991 |
| EP | 0 445 714 | | 9/1991 |
| EP | 0 503 507 | | 9/1992 |
| EP | 0 601 302 A1 | * | 4/1994 |
| FR | 2 189 380 | | 1/1974 |
| FR | 2 234 277 | | 1/1975 |
| FR | 2 382 232 | | 9/1978 |
| JP | 63-218614 | | 9/1988 |
| JP | 1-213221 | | 8/1989 |
| JP | 3-220114 | | 9/1991 |
| JP | 03220114 | * | 9/1991 |
| WO | WO 93/02655 | | 2/1993 |

OTHER PUBLICATIONS

English language translation of JP 63-218,614, pp. 1-17, Sep., 1988.
English language translation of JP 1-213,221, pp. 1-18, Aug., 1989.

* cited by examiner

*Primary Examiner*—Eisa Elhilo
(74) *Attorney, Agent, or Firm*—Finnegan, Henderson, Farabow, Garrett and Dunner, LLP

(57) ABSTRACT

The present invention relates to a composition comprising, in a cosmetically acceptable support suitable for dyeing the hair, at least one direct dye and at least one crosslinked polymer containing acrylic residue units of the structure $$CH_2=\underset{R_1}{\overset{}{C}}-\underset{O}{\overset{}{C}}-OH$$

in which $R_1$ denotes H, $CH_3$ or $C_2H_5$, and $C_{10}$–$C_{30}$ alkyl acrylate residue units, wherein the composition is a direct dyeing composition for the hair, and wherein said at least one direct dye is an anthraquinone or azo dye which is acidic or cationic.

4 Claims, No Drawings

DIRECT DYE COMPOSITION FOR THE HAIR, COMPRISING A CROSSLINKED POLYMER CONTAINING ACRYLIC UNITS AND C10-C30 ALKYL ACRYLATE UNITS

This application is a CIP of the U.S. application Ser. No. 09/068,964, filed on May 20, 1998 and now a U.S. Pat. No. 6,136,042 which is a 371 of PCT/FR97/00885 filed on May 20, 1997.

The invention relates to a composition for dyeing the hair, comprising at least one direct dye and at least one crosslinked polymer containing acrylic units and $C_{10}$–$C_{30}$ alkyl acrylate units.

It is known to dye hair fibres with direct dye compositions according to a so-called "direct dyeing" process which consists in applying to the fibres dye molecules which have an affinity for the said fibres, in leaving them to stand on the fibres and then in rinsing the fibres. The resulting colorations are temporary or semi-permanent colorations depending on the nature of the interactions between the direct dyes and the hair fibre, and their desorption from the surface and/or from the core of the fibre.

In order to facilitate the application of such dye compositions to the hair, in particular to prevent them from running down the forehead and the face or beyond the point of application initially chosen, when they are applied or during the exposure time required for dyeing, the viscosity of the compositions is conventionally increased using crosslinked polyacrylic acid (thickener). However, dye compositions based on direct dyes and on crosslinked polyacrylic acid no longer prove to be sufficiently satisfactory as regards their dyeing properties after they have been stored for a certain period at a temperature below room temperature, for example below 10° C., and in particular at about 4° C. Thus, it is observed that compositions stored under such conditions give rise to a weaker rise of the direct dye on the hair and thus have an insufficient dyeing power.

The present invention aims to solve the above problem, i.e. to propose a means which makes it possible to preserve the dyeing power of dye compositions containing a direct dye, for compositions liable to be stored at low temperatures, in particular at temperatures below 10° C.

After considerable research conducted in this matter, the Applicant has now discovered that it is possible to preserve the dyeing power of direct dye compositions if an effective amount of a crosslinked polymer containing acrylic units and $C_{10}$–$C_{30}$ alkyl acrylate units is added to these compositions.

Even after relatively prolonged storage at temperatures below 10° C., and in particular close to 4° C., compositions with good dyeing power and whose rise on the hair is very satisfactory are obtained.

This discovery forms the basis of the present invention.

The subject of the present invention is thus a cosmetic composition for dyeing the hair, of the type comprising, in a cosmetically acceptable support which is suitable for dyeing, at least one direct dye, characterized in that it also comprises at least one crosslinked polymer containing acrylic units and $C_{10}$–$C_{30}$ alkyl acrylate units.

The subject of the present invention is also the use of a crosslinked polymer containing acrylic units and $C_{10}$–$C_{30}$ alkyl acrylate units in, or for the manufacture of, a direct dye composition for the hair comprising at least one direct dye, in order to improve the conservation of the dyeing power of the said composition, in particular after storage below about 10° C., and especially at about 4° C.

The invention also relates to a process for improving the conservation of the dyeing power, in particular after storage below about 10° C., and especially at about 4° C., of a dye composition for the hair comprising at least one direct dye, this process consisting in introducing an effective amount of at least one crosslinked polymer containing acrylic units and $C_{10}$–$C_{30}$ alkyl acrylate units into the said composition.

Lastly, the invention relates to a process for dyeing hair using the compositions with improved properties in accordance with the invention.

However, other characteristics, aspects, objects and advantages of the invention will become even more apparent on reading the description and the examples which follow.

According to the invention, the term acrylic units is understood to denote units of structure

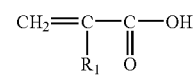

in which $R_1$ denotes H or $CH_3$ or $C_2H_5$, i.e. acrylic acid, methacrylic acid, or ethacrylic acid units.

The term alkyl acrylate units is also understood to denote units of structure:

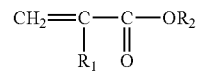

in which $R_1$ denotes H or $CH_3$ or $C_2H_5$, i.e. acrylate, methacrylate or ethacrylate units, $R_2$ denoting a $C_{10}$–$C_{30}$, preferably $C_{12}$–$C_{22}$, alkyl radical.

The crosslinked polymer(s) containing acrylic units and $C_{10}$–$C_{30}$ alkyl acrylate units, which can be used in the context of the present invention, can more particularly denote a terpolymer of a mixture of monomers essentially comprising:

(a) an acrylic, methacrylic or ethacrylic, but preferably acrylic or methacrylic, acid,
(b) an acrylate of formula:

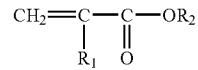

in which $R_1$ denotes H or $CH_3$ or $C_2H_5$, but preferably H or $CH_3$, and $R_2$ denotes an alkyl radical having from 10 to 30 carbon atoms, and preferably from 12 to 22 carbon atoms, and
(c) a crosslinking polymerizable monomer containing a group

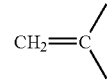

with at least one other polymerizable group in which the unsaturated bonds are not conjugated with each other.

Acrylates in accordance with the invention comprise, for example, lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate and dodecyl methacrylate.

Crosslinking polymerizable monomers of the type (c) are, for example, and preferably, polyallyl ethers such as, in particular, polyallylsucrose and polyallylpentaerythritol.

Crosslinked polymers of this type are well known; they are prepared and described in U.S. Pat. Nos. 3,915,921 and 4,509,949.

According to the invention, it is more particularly possible to use (i) those which consist of 95 to 60% by weight of acrylic units, from 4 to 40% by weight of acrylate units and from 0.1 to 6% by weight of crosslinking monomer of type (c) or (ii) those which consist of 98 to 96% by weight of acrylic units, from 1 to 4% by weight of acrylate units and from 0.1 to 0.6% by weight of crosslinking monomer of type (c).

Among the abovementioned crosslinked polymers, the products sold by the company Goodrich under the trade names Pemulen TR1, Pemulen TR2, Carbopol 1342, and even more preferably Pemulen TR1, are most particularly preferred according to the invention.

The crosslinked polymers containing acrylic units and $C_{10}$–$C_{30}$ alkyl acrylate units described above are used in the dye composition according to the invention in proportions which can range from about 0.05 to about 5% by weight, and preferably from about 0.1 to about 3% by weight, relative to the total weight of the composition.

The direct dyes which can be used in the dye composition according to the present invention are direct dyes in the sense defined above, that is to say dyes which can be used in a standard direct dyeing process.

Among those used conventionally, mention may be made of nitrobenzene dyes such as nitrophenylenediamines, nitrodiphenylamines, nitroanilines, nitrophenols or nitrophenol ethers, nitropyridines, anthraquinone, mono- or diazo, triarylmethane, azine, acridine and xanthene dyes or alternatively metalliferous dyes.

The direct dyes more particularly preferred according to the invention are chosen from the following:

i) the nitrobenzene dyes of formula (I) below:

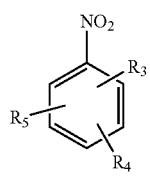

in which:
  $R_3$ denotes an $NH_2$ radical, an amino radical monosubstituted with an alkyl, monohydroxyalkyl, polyhydroxyalkyl or aminoalkyl radical, or an amino radical disubstituted with identical or different alkyl, mono- or polyhydroxyalkyl or aminoalkyl radicals,
  $R_4$ denotes hydrogen, hydroxyl, alkoxy, mono- or polyhydroxyalkyloxy, or the same meanings denoted above for $R_3$, except for the disubstituted amino radical,
  $R_5$ denotes hydrogen, alkyl, nitro or halogen, ii) the anthraquinone dyes of formula (II) below:

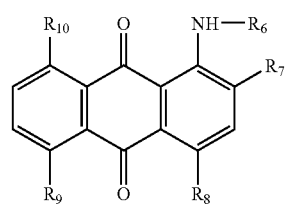

in which
  $R_6$ denotes hydrogen or a monohydroxyalkyl or polyhydroxyalkyl radical,
  $R_7$ denotes hydrogen or an alkyl or alkoxy radical,
  $R_1$ denotes hydrogen or a hydroxyl, amino, monohydroxyalkylamino or polyhydroxyalkylamino radical
  $R_9$ and $R_{10}$, which may be identical or different, are hydrogen, hydroxyl or amino, iii) the azo dyes of formula (III) below:

in which

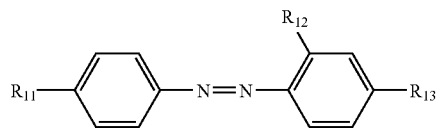

$R_{11}$ denotes a nitro or amino radical or an amino radical mono- or disubstituted with alkyls,
  $R_{12}$ denotes hydrogen or an alkyl radical,
  $R_{13}$ denotes an amino radical or an amino radical mono- or disubstituted with monohydroxyalkyls, it being understood that the alkyl and alkoxy radicals mentioned above in formulae (I), (II), and (III) are $C_1$–$C_4$ and that they can be linear or branched, and the cosmetically acceptable salts of all these compounds.

The term $C_1$–$C_4$ is understood to refer in particular to the methyl, ethyl, n-propyl, isopropyl, n-butyl, sec-butyl and tert-butyl radicals.

The expression cosmetically acceptable salts is understood more particularly to denote the hydrochlorides, hydrobromides and sulphates.

Even more advantageously, according to the present invention, it is preferred to use the following direct dyes:
  1-amino-2-nitro-4-N-(β-hydroxyethyl)amino-5-methylbenzene,
  1,4,5,8-tetraminoanthraquinone,
  1,4-bis-N-N'-[(β,γ-dihydroxypropyl)amino]-anthraquinone,
  1,4,4-N-tris(β-hydroxyethyl)-1,4-diamino-2-nitro-benzene,
  1-N-(β-hydroxyethyl)amino-2-nitro-4-aminobenzene,
  1-hydroxy-3-nitro-4-aminobenzene,
  1-hydroxy-3-nitro-4-N-(β-hydroxyethyl)aminobenzene,
  1-β-hydroxyethyloxy-3-methylamino-4-nitrobenzene,
  1-methylamino-2-nitro-5-β,γ-dihydroxypropyloxy-benzene,
  1-N-(β-aminoethyl)amino-2-nitro-4-β-hydroxyethyloxybenzene,
  4-[N-ethyl-N-(β-hydroxyethyl)amino]-1-N-(β-hydroxyethyl)amino-2-nitrobenzene,
  1-(4'-aminodiphenylazo)-2-methyl-4-N-bis(β-hydroxyethyl)aminobenzene,
  1-methoxy-3-N-(β-aminoethyl)amino-4-nitrobenzene, 1-amino-2-nitro-4-N-(β-hydroxyethyl)aminobenzene,
1-amino-2-nitro-4-N-bis(β-hydroxyethyl)aminobenzene,
1,4-N-bis(β-hydroxyethyl)amino-2-nitrobenzene,
1-amino-2-N-(β-hydroxyethyl)amino-5-nitrobenzene,
1,4-diaminoanthraquinone, and the cosmetically acceptable salts thereof.

The direct dyes may also be in the form of acid or cationic azo or anthraquinone dyes. In one embodiment of the present invention, the acid azo dyes are represented by formulae (I) and (I') below:

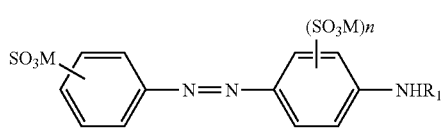
(I)

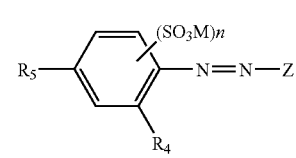
(I')

in which Z denotes (I')a or (I')b:

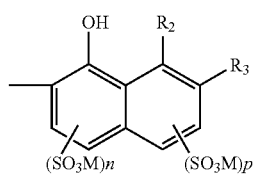
(I')a

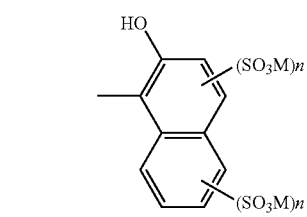
(I')b in which:
n denotes zero or 1,
p denotes zero, 1 or 2,
M denotes H or an alkali or alkaline-earth counterion, an organic amine which may be hydroxylated or not hydroxylated, or ammonia,
$R_1$ denotes H, $C_1$–$C_4$ alkyl radical or cycloalkylaryl radical,
$R_2$ denotes H, —$NH_2$, —HN—CO—$CH_3$, or —$NHSO_2$ phenyl radicals
$R_3$ denotes H, or a —N=N-(para-nitrophenyl) radical,
$R_4$ denotes a H, $C_1$–$C_4$ alkyl radical, $C_1$–$C_4$ alkoxyl radical, or forms a naphtalenyl ring with the adjacent carbon atom which is unsubstitued of the phenyl group,
$R_5$ denotes H, $C_1$–$C_4$ alkyl radical, $SO_3Na$, —$NH_2$, —HN—CO—$CH_3$, or —$NO_2$ radicals, and in which at least one —$SO_3M$ group is present in formulae (I), (I')a and (I')b.

The direct dyes may be in the form of cationic azo dyes represented by formulae (II), (III), (IV), (V), (VI), (VI'), (VII) and their mesomeric forms. These dyes can be chosen from the following:
(i) dyes of formulae (II) and (III) below:

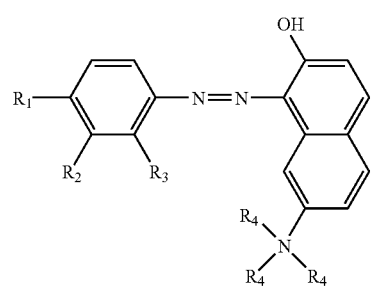
(II)

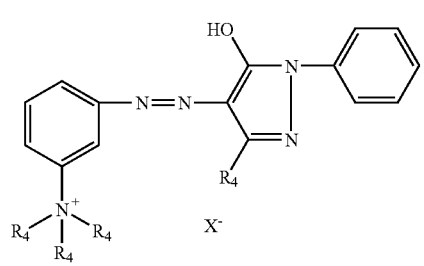
(III)

in which:
$R_1$ denotes H or —$NH_2$,
$R_2$ denotes H or —$NO_2$
$R_3$ denotes H or —$NO_2$ or an $C_1$–$C_4$ alkoxyl radical
$R_4$ denotes a $C_1$–$C_4$ alkyl radical,
$X^-$ denotes an anion preferably chosen from chloride, methyl sulphate and acetate;
(ii) dyes of formulae (IV), (V), (VI), (VI'), (VII) below:
a) the compounds of formula (IV) below:

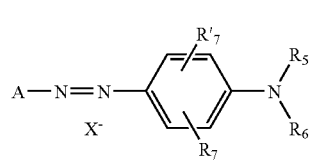
(IV)

in which:
$R_5$ and $R_6$, which may be identical or different, denote a hydrogen atom, $C_1$–$C_4$ alkyl radicals which can have a substituent chosen from —CN, —OH and —$NH_2$ radicals, and a 4'-aminophenyl radical, or form, with a carbon atom of the benzene ring, a heterocycle, oxygenated and/or nitrogenated and optionally having at least one substituent chosen from $C_1$–$C_4$ alkyl radicals,
$R_7$ and $R'_7$ which may be identical or different, denote a hydrogen atom, halogen atoms chosen from chlorine, bromine, iodine and fluorine, and cyano, $C_1$–$C_4$ alkyl, $C_1$–$C_4$ alkoxy, or acetyloxy radicals,
$X^-$ denotes an anion preferably chosen from chloride, methyl sulphate and acetate;

A is a group chosen from structures $A_1$ to $A_{19}$ below:
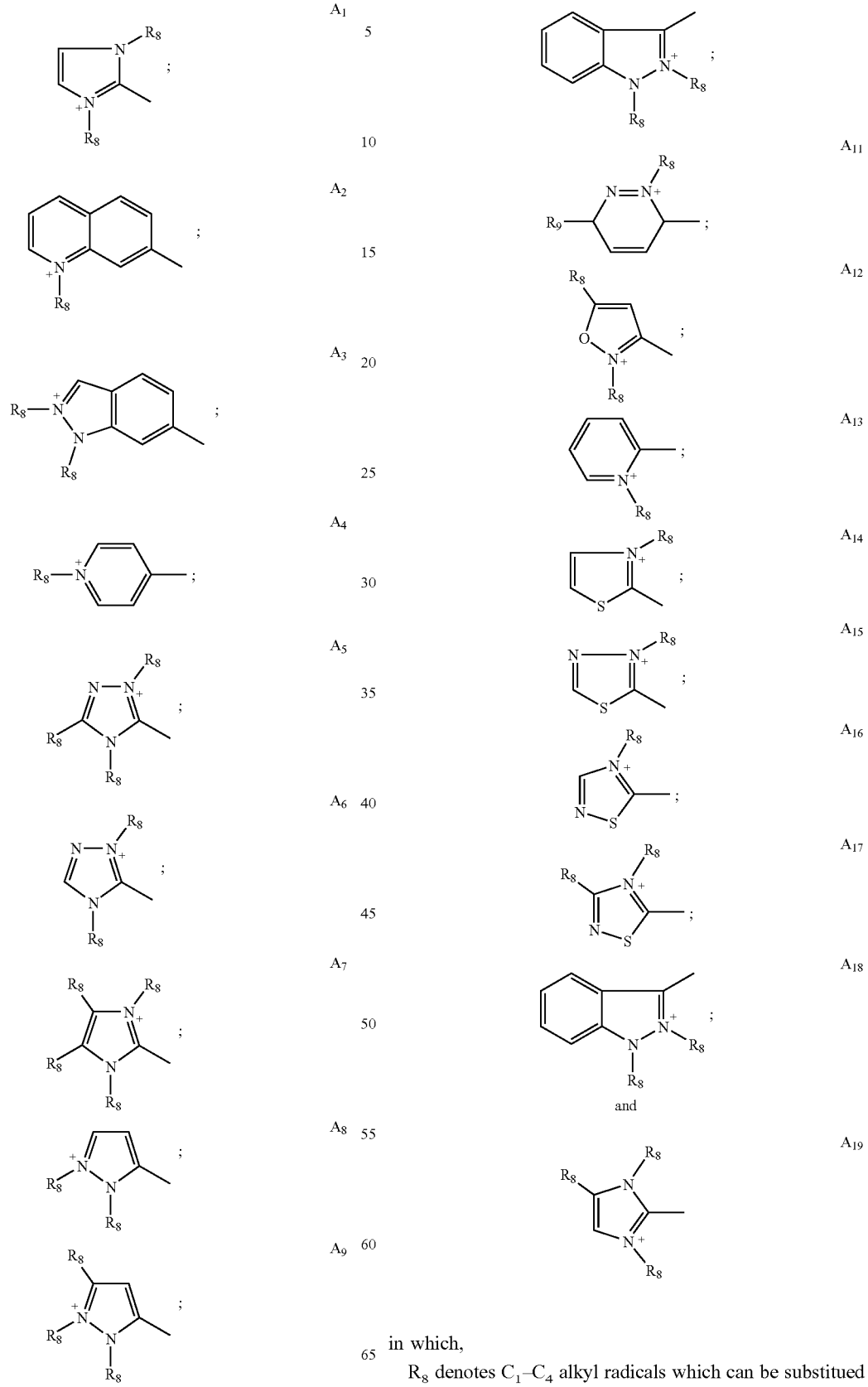
in which,
$R_8$ denotes $C_1$–$C_4$ alkyl radicals which can be substitued with a hydroxyl radical and $R_9$ denotes $C_1$–$C_4$ alkoxy radicals, b) the compounds of formula (V) below:

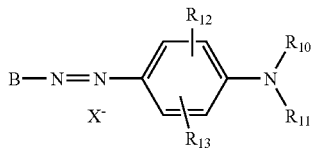
(V)

in which:

$R_{10}$ denotes hydrogen or $C_1$–$C_4$ alkyl radicals, $R_{11}$ denotes hydrogen or $C_1$–$C_4$ alkyls optionally having a substituent chosen from —CN and amino radicals, and a 4'-aminophenyl radical, or forms with $R_{10}$ a heterocycle, oxygenated and/or nitrogenated and optionally having at least one substituent chosen from $C_1$–$C_4$ alkyl radicals, $R_{12}$ and $R_{13}$, which may be identical or different, denote a hydrogen atom, halogen atoms, such as bromine, chlorine, iodine or fluorine, $C_1$–$C_4$ alkyl, $C_1$–$C_4$ alkoxy, or —CN radicals, $X^-$ denotes an anion preferably chosen from chloride, methyl sulphate and acetate;

B is a group chosen from structures B1 to B6 below:

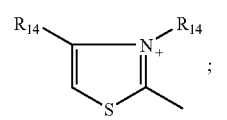
B1

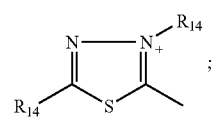
B2

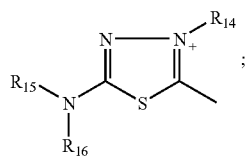
B3

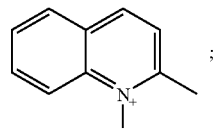
B4

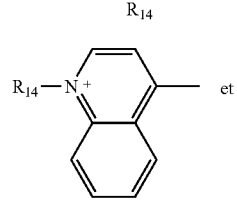
B5

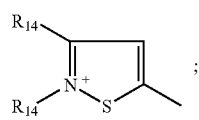
B6 in which, $R_{14}$ denotes $C_1$–$C_4$ alkyl radicals, and $R_{15}$ and $R_{16}$, which may be identical or different, denote a hydrogen atom or $C_1$–$C_4$ alkyl radicals;

c) the compounds of formulae (VI) and (VI') below:

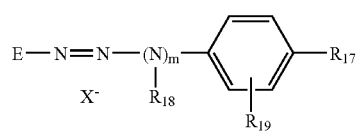
(VI)

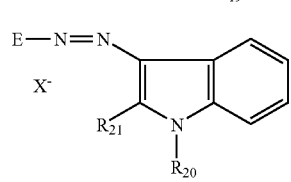
(VI')

in which:

$R_{17}$ denotes a hydrogen atom, $C_1$–$C_4$ alkoxy radicals, halogen atoms, such as bromine, chlorine, iodine and fluorine, or unsubstitued and substitued amino radicals, $R_{18}$ denotes a hydrogen atom, $C_1$–$C_4$ alkyl radicals, or forms with a carbon atom of the benzene ring, a heterocycle which is optionally oxygenated and optionally having at least a substituent chosen from $C_1$–$C_4$ alkyl radicals, $R_{19}$ denotes a hydrogen atom and halogen atoms, such as bromine, chlorine, iodine and fluorine, $R_{20}$ and $R_{21}$, which may be identical or different, denote a hydrogen atom and $C_1$–$C_4$ alkyl radicals, m is zero or 1, $X^-$ denotes an anion preferably chosen from chloride, methyl sulphate and acetate;

E is a group chosen from structures E1 to E8 below:

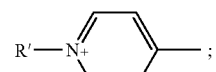
E1

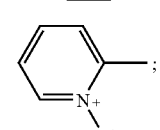
E2

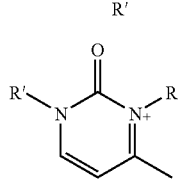
E3

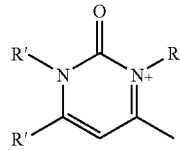
E4

-continued

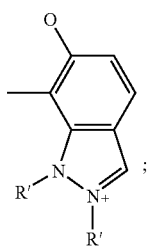
E5

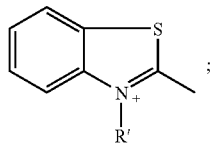
E6

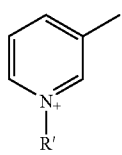
E7 and

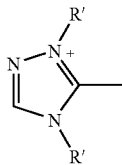
E8 in which,
R' denotes $C_1$–$C_4$ alkyl radicals,
when m is 0, then E can also be a group of structure E9 below:

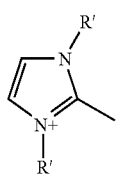
E9 in which,
R' denotes $C_1$–$C_4$ alkyl radicals.
d) the compounds of formula (VII) below:

    (VII)

in which, the symbol G represents a group chosen from structures G1 to G3 below:

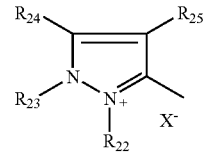
$G_1$

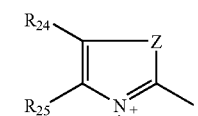
$G_2$

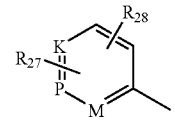
$G_3$ in which,
$R_{22}$ denotes $C_1$–$C_4$ alkyl radicals or a phenyl radical optionally having a substituent chosen from $C_1$–$C_4$ alkyl radicals and halogen atoms chosen from chlorine, bromine, iodine and fluorine, $R_{23}$ denotes $C_1$–$C_4$ alkyl radicals or a phenyl radical, $R_{24}$ and $R_{25}$, which may be identical or different, denote $C_1$–$C_4$ alkyl radicals or a phenyl radical or, in the case of structure $G_1$, can together form a benzene ring having at least one substituent chosen from $C_1$–$C_4$ alkyl, $C_1$–$C_4$ alkoxy and $NO_2$ radicals, and in the case of structure $G_2$, can together form a benzene ring optionally having at least one substituent chosen from $C_1$–$C_4$ alkyl, $C_1$–$C_4$ alkoxy and $NO_2$ radicals, $R_{24}$ can also denote a hydrogen atom, Z denotes an oxygen atom, a sulphur atom or —$NR_{23}$ groups;

M denotes —CH, —CR where R is chosen from $C_1$–$C_4$ alkyl radicals or —$NR_{26}(X^-)_r$ groups, wherein r is zero or 1, K denotes —CH, —CR where R is chosen from $C_1$–$C_4$ alkyl radicals, or —$NR_{26}(X^-)_r$ groups wherein r is zero or 1, P denotes —CH, —CR where R is chosen from $C_1$–$C_4$ alkyl radicals, or —$NR_{26}(X^-)_r$ groups wherein r is zero or 1, $R_{26}$ denotes an oxygen atom, $C_1$–$C_4$ alkoxy radicals or $C_1$–$C_4$ alkyl radicals, $R_{27}$ and $R_{28}$, which may be identical or different, denote a hydrogen atom, a halogen atom chosen from chlorine, bromine, iodine and fluorine, $C_1$–$C_4$ alkyl radicals, $C_1$–$C_4$ alkoxy radicals and an —$NO_2$ radical, $X^-$ denotes an anion, preferably chosen from chloride, iodide, methyl sulphate, ethyl sulphate, acetate and perchlorate, and wherein at least one of K, M or P denotes —$NR_{26}(X^-)_r$, and wherein the symbol J represents:
(a) a group of structure $J_1$ below:

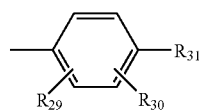 $J_1$ in which,

- $R_{29}$ denotes a hydrogen atom, a halogen atom chosen from chlorine, bromine, iodine and fluorine, $C_1$–$C_4$ alkyl radicals, $C_1$–$C_4$ alkoxy radicals, a radical —OH, a radical —$NO_2$, —$NHR_{32}$ radicals, —$NR_{33}R_{34}$ radicals, —NHCO($C_1$–$C_4$)alkyl radicals, or forms with $R_{30}$ a 5- or 6-membered ring which may contain at least one hetero atom chosen from nitrogen, oxygen and sulphur;
- $R_{30}$ denotes a hydrogen atom, a halogen atom chosen from chlorine, bromine, iodine and fluorine, $C_1$–$C_4$ alkyl radicals, $C_1$–$C_4$ alkoxy radicals, or forms, with $R_{31}$ or $R_{32}$, a 5- or 6-membered ring which may contain at least one hetero atom chosen from nitrogen, oxygen and sulphur;
- $R_{31}$ denotes a hydrogen atom, an —OH radical, —$NHR_{32}$ radicals or —$NHR_{33}R_{34}$ radicals;
- $R_{32}$ denotes a hydrogen atom, $C_1$–$C_4$ alkyl radicals, $C_1$–$C_4$ monohydroxyalkyl radicals, $C_2$–$C_4$ polyhydroxyalkyl radicals or a phenyl radical;
- $R_{33}$ and $R_{34}$, which may be identical or different, denote $C_1$–$C_4$ alkyl radicals, $C_1$–$C_4$ monohydroxyalkyl radicals or $C_2$–$C_4$ polyhydroxyalkyl radicals;

(b) a 5- or 6-membered nitrogenous heterocyclic group which can contain at least one other hetero atom and/or at least one carbonyl group and which can have at least one substituent chosen from $C_1$–$C_4$ alkyl, amino or phenyl radicals, and in particular a group of structure $J_2$ below:

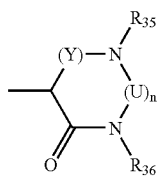 $J_2$ in which,

- $R_{35}$ and $R_{36}$, which may be identical or different, denote a hydrogen atom, $C_1C_4$ alkyl or phenyl radicals,
- Y denotes a —CO— radical or a radical

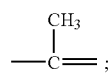

n=0 or 1, where, when n denotes 1, U denotes a —CO— radical.

The direct dyes may also be in the form of acidic or cationic anthraquinonic dyes. The preferred acid anthraquinonic dyes are represented by formulae (VIII) below:

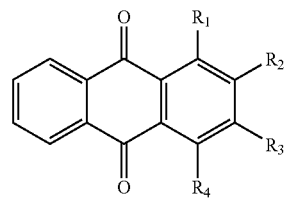 (VIII)

in which:

- $R_1$ denotes a hydrogen atom, a —$NH_2$ radical, or a —$NHR_5$ radical, as defined below,
- $R_2$ denotes a hydrogen atom or a —$SO_3M$ radical where M denotes H or an alkaline or alkaline-earth counterion, an organic amine which may be hydroxylated or not hydroxylated, or ammonia,
- $R_3$ denotes a hydrogen atom or a —OH radical,
- $R_4$ denotes a —$NHR_6$, —OH, or —$NHR_5$ radical,
- $R_5$ denotes a radical of structure below:

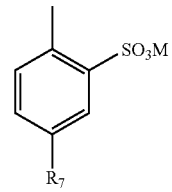

in which $R_7$ represents a $C_1$–$C_4$ alkyl radical,
$R_6$ denotes a linear or cyclic $C_1$–$C_6$ alkyl radical,
and in which formula (VIII), at least one —$SO_3M$ radical is present.

The cationic anthraquinonic dyes are represented by formula (IX) below:

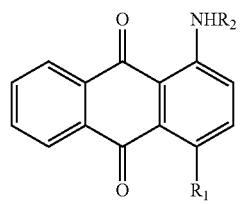 (IX)

in which:

- $R_1$ denotes a hydrogen atom, a —OH radical, a —$NH_2$ radical, or a —NH($C_1$–$C_4$)alkyl radical,
- $R_2$ denotes a —$(CH_2)_n$—$NR_3R_4(R_5)_m$— radical, in which n denotes 1 or 10, m denotes zero or 1, and
- $R_3$, $R_4$, $R_5$ which may be identical or different, denotes a hydrogen atom or a $C_1$–$C_4$ alkyl radical, and wherein $R_3$ and $R_4$, with the nitrogenous atom, can form a 5- or 6-membered heterocycle group which can contain at least one other hetero atom chosen from nitrogen, oxygen or sulphur and optionally having at least one substituent chosen from $C_1$–$C_4$ alkyl radicals, amino radicals, and phenyl radicals.

These direct dyes, are generally present in the dye composition according to the invention in proportions which can range from about 0.001 to about 10% by weight, and preferably from about 0.05 to about 5% by weight, relative to the total weight of the composition.

The cosmetically acceptable medium for the dyeing is an aqueous medium which can contain one or more organic solvents chosen, for example, from ethyl alcohol, isopropyl alcohol, benzyl alcohol and phenylethyl alcohol, or glycols or glycol ethers such as, for example, propylene glycol or its ethers such as, for example, propylene glycol monomethyl ether, butylene glycol, dipropylene glycol, ethylene glycol monomethyl, monoethyl and monobutyl ethers, and diethylene glycol alkyl ethers such as, for example, diethylene glycol monoethyl ether or monobutyl ether, in proportions of approximately between 0.5 and 20% by weight, and preferably approximately between 2 and 10% by weight, relative to the total weight of the composition.

Fatty amides such as mono- and diethanolamides of coconut-derived acids, of lauric acid or of oleic acid, at concentrations of approximately between 0.05 and 10% by weight can also be added to the composition according to the invention.

Surfactants that are well known in the state of the art and of anionic, cationic, nonionic, amphoteric or zwitterionic type or mixtures thereof can also be added to the composition according to the invention, preferably in a proportion of approximately between 0.1 and 50% by weight, and advantageously approximately between 1 and 20% by weight, relative to the total weight of the composition.

The said dye composition can also contain various common adjuvants such as antioxidants, fragrances, sequestering agents, dispersing agents, hair conditioners, preserving agents and opacifiers, as well as any other adjuvant usually used to dye the hair.

Needless to say, a person skilled in the art will take care to select the optional complementary compound(s) mentioned above such that the advantageous properties intrinsically associated with the dye composition according to the invention are not, or are not substantially, adversely affected by the addition(s) envisaged.

The dye composition according to the invention can be formulated at acidic, neutral or alkaline pH, it being possible for the pH to vary, for example, from 3 to 12 and preferably from 7 to 11 and even more preferably from 8.5 to 10, and for it be adjusted using basifying agents or acidifying agents that are previously well known. As basifying agents, mention may be made of aqueous ammonia, alkaline carbonates, alkanolamines, for example mono-, di- and triethanolamines and derivatives thereof, sodium hydroxide, potassium hydroxide, and compounds of formula:

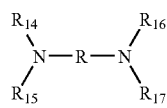

in which R is a propylene residue optionally substituted with a hydroxyl group or a $C_1$–$C_4$ alkyl radical; $R_{14}$, $R_{15}$, $R_{16}$ and $R_{17}$, simultaneously or independently of each other, represent a hydrogen atom or a $C_1$–$C_4$ alkyl or $C_1$–$C_4$ hydroxyalkyl radical.

The acidifying agents are conventionally inorganic or organic acids such as, for example, hydrochloric acid, tartaric acid, citric acid and phosphoric acid.

The composition applied to the hair can be in various forms, such as in the form of a liquid, a cream or a gel or in any other form which is suitable for dyeing the hair. In particular, it can be packaged under pressure in an aerosol can in the presence of a propellant and can form a mousse.

Another subject of the present invention relates to a process for dyeing the hair, by direct dyeing, which consists in applying a dye composition as defined above to wet or dry hair, then in leaving the said composition to act, preferably for 3 to 60 minutes approximately, in rinsing the hair, then optionally in washing it, then in rinsing it again and then in drying it.

It is also possible to leave the composition to act and then dry it.

Concrete examples illustrating the invention will now be given.

EXAMPLE 1

The following dyeing composition was prepared:

| | |
|---|---|
| Direct dye (1)* | 0.1 g |
| Decyl alcohol oxyethylenated with 5.3 mol of ethylene oxide | 2.0 g |
| Lauric acid | 1.0 g |
| Diethylene glycol monobutyl ether | 5.0 g |
| Pemulen TR1 from Goodrich (acrylic acid/$C_{10}$–$C_{30}$ alkyl acrylates crosslinked copolymer) | 0.51 g |
| 2-Amino-2-methyl-1-propanol q.s. pH | 9.5 |
| Demineralized water q.s. p | 100 g |

*dye (1): 1-amino-2-nitro-4-N-(β-hydroxyethyl)amino-5-methylbenzene

After 24 hours, the viscosity of this composition was measured using a Contrave viscometer at 25° C. The viscosity recorded was 200 cp.

This composition was then applied to locks of natural grey hair containing 90% white hairs and the composition was left to stand on the hair for 30 minutes. The locks were then rinsed with running water and dried.

The locks were dyed in a shade which, quantified in terms of the Munsell value (ASTM standard D 1535-68, which defines the colour: H denoting the shade or Hue, V denoting the intensity or Value, and C denoting the purity or Chromacity), on a Minolta CM 2002 colorimeter, was as follows:

in H,V,C, 7.5 R 4.7/2.9.

The control locks (not dyed) had an H,V,C shade: 3.8 Y 5.7/1.6.

The composition prepared above was also stored for one month at a temperature of 4° C.

The composition thus stored was then applied to locks of hair of the same quality and according to the same procedure as above.

The shade of the locks dyed using this composition stored at 4° C. was as follows: in H,V,C, 7.9 R 4.7/2.8.

The change in colour between the locks dyed using the initial composition and those dyed using the composition stored for one month at a temperature of 4° C. was then quantified using the Nickerson equation which defines the colour variation indices: $I=(C/5)\times 2\Delta H+6\Delta V+3\Delta C$ (this equation being described in the publication: "Journal of the Optical Society of America", 1944-September. Vol. 34, No. 9, pp. 550–570).

Thus, the change in Colour Ib (colour variation index between the locks dyed using the composition stored for one month at a temperature of 4° C. and that of the locks dyed using the initial composition) relative to the initial coloration $I_a$ (colour variation index of the locks dyed using the initial composition and that of the control locks), quantified in %, was 3.7%.

COMPARATIVE EXAMPLE 2

A dye composition similar to that of Example 1 was prepared, with a viscosity equal to that of Example 1, based on polymer of the prior art, but simply replacing the 0.51 g of Pemulen TR1 by 0.57 g of Carbopol 980 from the company Goodrich (crosslinked polyacrylic acid of the prior art—MW 4,000,000).

Locks of natural hair containing 90% white hairs were dyed using the initial composition (i.e. before storage) and according to a procedure identical to that of Example 1, in a shade, expressed in terms of H,V,C, equal to: 8.1 R 4.9/2.9. Locks of natural hair containing 90% white hairs were dyed using the same composition but stored for one month at 4° C. The shade obtained was: H,V,C, 8.7 R 4.8/2.8.

The ratio $I_b/I_a$ applied to this example, and quantified in %, was 8.5%.

Conclusion

After storage for one month at 4° C., the dye composition of Example 1 comprising a crosslinked polymer in accordance with the present invention has a dyeing power which is considerably superior to that of the dye composition of Example 2 comprising a crosslinked polymer of the prior art, since the degradation, which is expressed by the ratio $I_b/I_a$, quantified in %, is only 3.7% in the case of Example 1, whereas it is 8.5% in the case of Example 2.

EXAMPLE 3

The following dye composition was prepared:

| | |
|---|---|
| Direct dye (2)* | 0.1 g |
| Decyl alcohol oxyethylenated with 5.3 mol of ethylene oxide | 2.0 g |
| Lauric acid | 1.0 g |
| Diethylene glycol monobutyl ether | 5.0 g |
| Pemulen TR1 from Goodrich (acrylic acid/$C_{10}$–$C_{30}$ alkyl acrylates crosslinked copolymer) | 0.54 g |
| 2-Amino-2-methyl-1-propanol q.s. pH | 9.5 |
| Demineralized water q.s. p | 100 g |

*direct dye (2): 1,4,5,8-tetraaminoanthraquinone (at 30%, dispersed on lignosulphate)

After 24 hours, the viscosity of this composition was measured using a Contrave viscometer at 25° C. The viscosity recorded was 220 cp.

This composition was then applied to locks of permanent-waved grey hair containing 90% white hairs and the composition was left to stand on the hair for 30 minutes. The locks were then rinsed with running water and dried.

The locks were dyed in a shade which, quantified in terms of the Munsell value, was as follows, in H,V,C, 4.1 B 4.2/2.4.

The control locks (not dyed) had an H,V,C shade: 4.4 Y 5.9/1.6.

The abovementioned composition was then stored for one month at a temperature of 4° C.

The composition thus stored was then applied to locks of hair of the same quality and according to the same procedure as above.

The shade of the locks dyed using this composition stored at 4° C. was as follows, in terms of H,V,C, 2.1 B 4.4/2.2.

The ratio $I_b$ (colour variation index between the locks dyed using the composition stored for one month at a temperature of 4° C. and that of the locks dyed using the initial composition) to $I_a$ (colour variation index between the locks dyed using the initial composition and that of the control locks), quantified in %, was 9.8%.

COMPARATIVE EXAMPLE 4

A dye composition similar to that of Example 3 was prepared, with a viscosity equal to that of Example 3, based on polymer of the prior art, but simply replacing the 0.54 g of Pemulen TR1 by 0.67 g of Carbopol 2984 from the company Goodrich (crosslinked polyacrylic acid of the prior art—MW 3,000,000).

Locks of permanent-waved hair containing 90% white hairs were dyed using the initial composition (i.e. before storage) and according to a procedure identical to that of Example 3, in a shade, expressed in terms of H,V,C, equal to: 5.4 B 4.1/3.1.

Locks of permanent-waved hair containing 90% white hairs were dyed using the same composition but stored for one month at 4° C. The shade obtained was, in terms of H, V, C, equal to: 1.6 B 4.3/1.9.

The ratio $I_b/I_a$ applied to this example, and quantified in %, was 22.9%.

Conclusion:

After storage for one month at 4° C., the dye composition of Example 3 comprising a crosslinked polymer in accordance with the present invention has a dyeing power which is considerably superior to that of the dye composition of Example 4 comprising a crosslinked polymer of the prior art, since the degradation, which is expressed by the ratio $I_b/I_a$, quantified in %, is only 9.8% in the case of Example 3, whereas it is 22.9% in the case of Example 4.

EXAMPLE 5

The following dye composition was prepared:

| | |
|---|---|
| Direct dye (3)* | 0.15 g |
| Decyl alcohol oxyethylenated with 5.3 mol of ethylene oxide | 2.0 g |
| Lauric acid | 1.0 g |
| Diethylene glycol monobutyl ether | 5.0 g |
| Pemulen TR1 from Goodrich (acrylic acid/$C_{10}$–$C_{30}$ alkyl acrylates crosslinked copolymer) | 0.52 g |
| 2-Amino-2-methyl-1-propanol q.s. pH | 9.5 |
| Demineralized water q.s. p | 100 g |

*direct dye (3): 1,4-bis-N,N'-[(β,γ-dihydroxypropyl)amino]anthraquinone.

After 24 hours, the viscosity of this composition was measured using a Contrave viscometer at 25° C. The viscosity recorded was 210 cp.

This composition was then applied to locks of natural grey hair containing 90% white hairs and was left to stand on the hair for 30 minutes. The locks were then rinsed with running water and dried.

The locks were dyed in a shade which, quantified in terms of the Munsell value, was as follows, in terms of H,V,C, 5.9 GY 5.1/1.0.

The control locks (not dyed) had an H,V,C shade: 3.8 Y 5.7/1.6.

The abovementioned composition was then stored for one month at a temperature of 4° C.

The composition thus stored was then applied to locks of hair of the same quality and according to the same procedure as above.

The shade of the locks dyed using this composition stored at 4° C. was as follows, in terms of H,V,C, 1.2 GY 5.1/1.1.

The ratio $I_b$ (colour variation index between the locks dyed using the composition stored for one month at a temperature of 4° C. and that of the locks dyed using the initial composition) to $I_a$ (colour variation index between the locks dyed using the initial composition and that of the control locks), quantified in %, was 16.6%.

COMPARATIVE EXAMPLE 6

A dye composition similar to that of Example 5 was prepared, with a viscosity equal to that of Example 5, based on polymer of the prior art, but simply replacing the 0.52 g of Pemulen TR1 by 0.65 g of Carbopol 2984 from the company Goodrich (crosslinked polyacrylic acid of the prior art).

Locks of natural hair containing 90% white hairs were dyed using the initial composition (i.e. before storage) and according to a procedure identical to that of Example 5, in a shade, expressed in terms of H,V,C, equal to: 6.6 GY 5.2/1.0.

Locks of natural hair containing 90% white hairs were dyed using the same composition but stored for one month at 4° C. The shade obtained was, in terms of H,V,C, equal to: 10.0 Y 5.4/1.2.

The ratio $I_b/I_a$ applied to this example, and quantified in %, was 34.2%.

Conclusion

After storage for one month at 4° C., the dye composition of Example 5 comprising a crosslinked polymer in accordance with the present invention has a dyeing power which is considerably superior to that of the dye composition of Example 6 comprising a crosslinked polymer of the prior art, since the degradation, which is expressed by the ratio $I_b/I_a$, quantified in %, is only 16.6% in the case of Example 5, whereas it is 34.2% in the case of Example 6.

I claim:

1. A composition comprising, in a cosmetically acceptable support suitable for dyeing the hair, at least one direct dye and at least one crosslinked polymer containing acrylic residue units of the structure

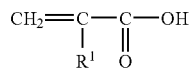

in which $R_1$ denotes H, $CH_3$ or $C_2H_5$, and $C_{10}$–$C_{30}$ alkyl acrylate residue units, wherein said composition is a direct dyeing composition for the hair, wherein said at least one direct dye is an acid azo dye of formulae (I) or (I'):

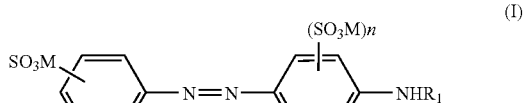

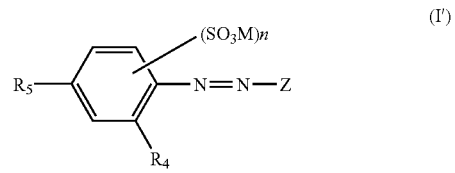

in which Z denotes (I')a or (I')b:

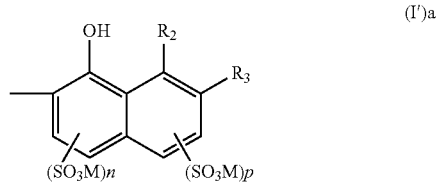

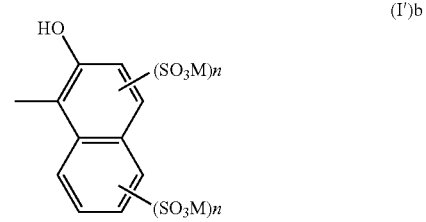

in which:
 n denotes zero or 1,
 p denotes zero, 1 or 2,
 M denotes H or an alkali or alkaline-earth counterion, an organic amine which may be hydroxylated or not hydroxylated, or ammonia,
 $R_1$ denotes H, a $C_1$–$C_4$ alkyl radical or an cycloalkylaryl radical,
 $R_2$ denotes H, an —$NH_2$ radical, an —HN—CO—$CH_3$ radical or an —$NHSO_2$-phenyl radical,
 $R_3$ denotes H, or a —N=N-(para-nitrophenyl) radical,
 $R_4$ denotes a H, a $C_1$–$C_4$ alkyl radical, a $C_1$–$C_4$ alkoxyl radical, or forms a naphtalenyl ring with the adjacent carbon atom which is unsubstitued of the phenyl group,
 $R_5$ denotes H, a $C_1$–$C_4$ alkyl radical, an —$SO_3Na$ radical, a —$NH_2$ radical, an —HN—CO—$CH_3$ radical or an —$NO_2$ radical, and in which at least one —$SO_3M$ group is present in formulae (I), (I')a and (I')b
with the proviso that at least one direct dye is not a dye of chemical formula:

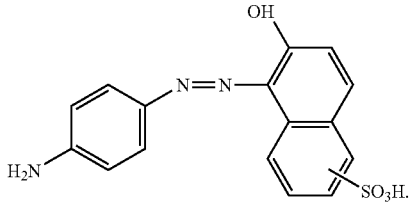

2. A composition comprising, in a cosmetically acceptable support suitable for dyeing the hair, at least one direct dye and at least one crosslinked polymer containing acrylic residue units of the structure

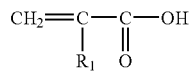

in which $R_1$ denotes H, $CH_3$ or $C_2H_5$, and $C_{10}$–$C_{30}$ alkyl acrylate residue units, wherein said composition is a direct dyeing composition for the hair, wherein said at least one direct dye is a cationic azo dye of formulae (II), (III), (IV), (V), (VI), (VI'), (VII) and their mesomeric forms, wherein (i) dyes of formulae (II) and (III) are:

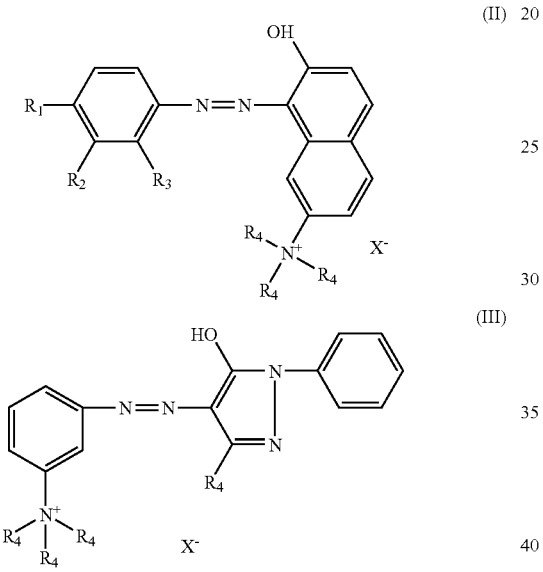

in which
$R_1$ denotes H or an —$NH_2$ radical,
$R_2$ denotes H or a —$NO_2$ radical,
$R_3$ denotes H or a —$NO_2$ radical or an $C_1$–$C_4$ alkoxyl radical,
$R_4$ denotes a $C_1$–$C_4$ alkyl radical,
$X^-$ denotes an anion chosen from chloride, methyl sulphate and acetate, wherein;

(ii) dyes of formulae (IV), (V), (VI), (VI'), (VII) include:
a) the compounds of formula (IV):

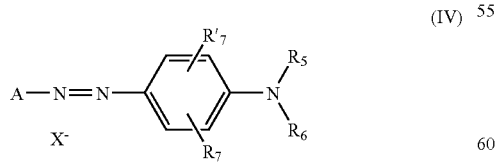

in which:
$R_5$ and $R_6$, which may be identical or different, denote a hydrogen atom, $C_1$–$C_4$ alkyl radicals which can have a substituent chosen from —CN, —OH and —$NH_2$ radicals, and a 4'-aminophenyl radical, or form, with a carbon atom of the benzene ring, a heterocycle, oxygenated and/or nitrogenated and optionally having at least one substituent chosen from $C_1$–$C_4$ alkyl radicals, $R_7$ and $R'_7$ which may be identical or different, denote a hydrogen atom, a halogen atom chosen from chlorine, bromine, iodine and fluorine, a cyano radical, a $C_1$–$C_4$ alkyl radical, a $C_1$–$C_4$ alkoxy radical, or an acetyloxy radical, $X^-$ denotes an anion chosen from chloride, methyl sulphate and acetate;

A is a group chosen from structures $A_1$ to $A_{19}$:

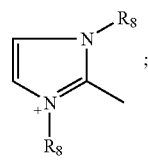

$A_1$

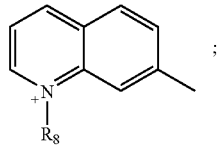

$A_2$

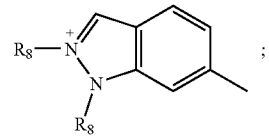

$A_3$

$A_4$

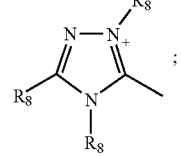

$A_5$

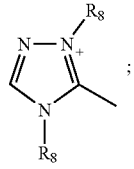

$A_6$

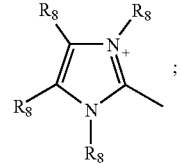

$A_7$

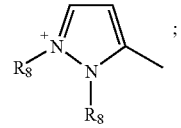

$A_8$

-continued

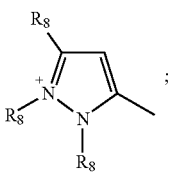 A9

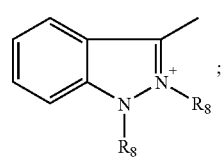 A10

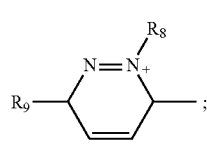 A11

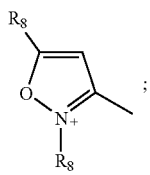 A12

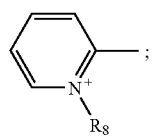 A13

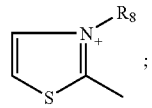 A14

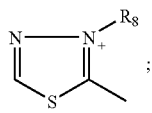 A15

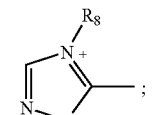 A13

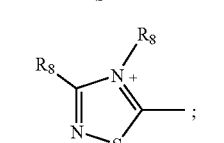 A14

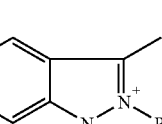 A15

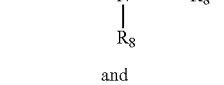

and

-continued

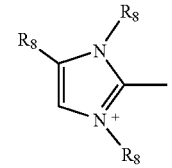 A19 in which,
R8 denotes a $C_1$–$C_4$ alkyl radical which can be substitued with a hydroxyl radical and
R9 denotes a $C_1$–$C_4$ alkoxy radical,
b) the compounds of formula (V):

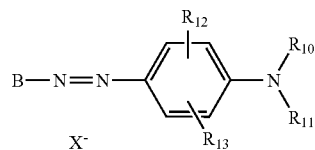 (V)

in which:
$R_{10}$ denotes hydrogen or a $C_1$–$C_4$ alkyl radical,
$R^{11}$ denotes hydrogen or a $C_1$–$C_4$ alkyl radical optionally having a substituent chosen from a —CN radical, an amino radical, and a 4'-aminophenyl radical, or forms with $R_{10}$ a heterocycle, oxygenated and/or nitrogenated and optionally having at least one substituent chosen from a $C_1$–$C_4$ alkyl radical,
$R_{12}$ and $R_{13}$, which may be identical or different, denote a hydrogen atom, a halogen atom chosen from bromine, chlorine, iodine or fluorine, a $C_1$–$C_4$ alkyl radical, a $C_1$–$C_4$ alkoxy radical, or a —CN radical,
$X^-$ denotes an anion chosen from chloride, methyl sulphate and acetate;
B is a group chosen from structures B1 to B6:

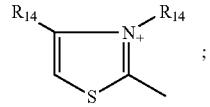 B1

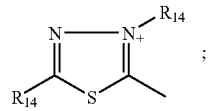 B2

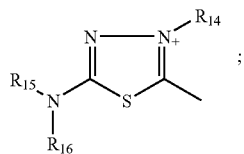 B3

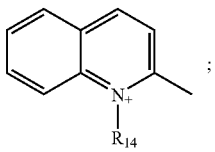 B4

-continued

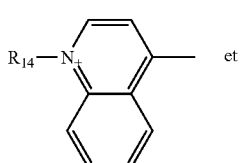
B5

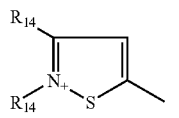
B6 in which,
R_{14} denotes a $C_1$–$C_4$ alkyl radical, and
R_{15} and R_{16}, which may be identical or different, denote a hydrogen atom or a $C_1$–$C_4$ alkyl radical;
c) the compounds of formulae (VI) and (VI'):

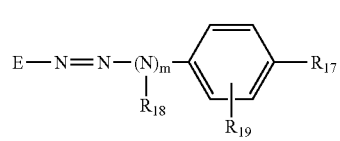
(VI)

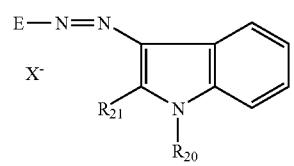
(VI')

in which:
R_{17} denotes a hydrogen atom, a $C_1$–$C_4$ alkoxy radical, a halogen atom chosen from bromine, chlorine, iodine and fluorine, an unsubstitued amino radical, or a substitued amino radical,
R_{18} denotes a hydrogen atom, a $C_1$–$C_4$ alkyl radical, or forms with a carbon atom of the benzene ring, a heterocycle which is optionally oxygenated and optionally having at least a substituent chosen from a $C_1$–$C_4$ alkyl radical,
R_{19} denotes a hydrogen atom or a halogen atom chosen from bromine, chlorine, iodine and fluorine,
R_{20} and R_{21}, which may be identical or different, denote a hydrogen atom or a $C_1$–$C_4$ alkyl radical,
m is zero or 1,
$X^-$ denotes an anion chosen from chloride, methyl sulphate and acetate; E is a group chosen from structures E1 to E8:

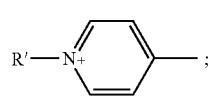
E1

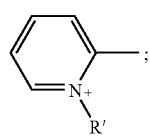
E2

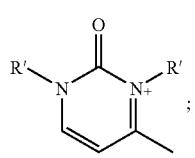
E3

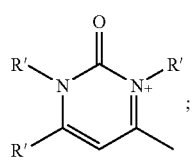
E4

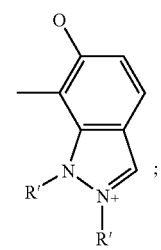
E5

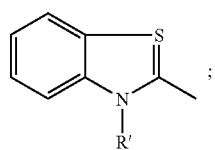
E6

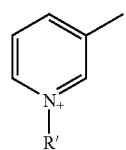
E7 and

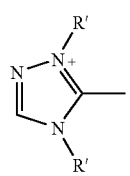
E8 in which
R' denotes a $C_1$–$C_4$ alkyl radical,
when m is 0, then E can also be a group of structure E9:

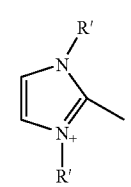
E9 in which,
R' denotes a $C_1$–$C_4$ alkyl radical,
d) the compounds of formula (VII):

$$G\text{—}N\text{=}N\text{—}J \qquad (VII)$$

in which,
the symbol G represents a group chosen from structures $G_1$ to $G_3$:

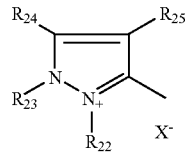
$G_1$

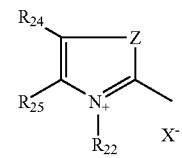
$G_2$

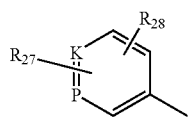
$G_3$ in which,
$R_{22}$ denotes a $C_1$–$C_4$ alkyl radical or a phenyl radical optionally having a substituent chosen from a $C_1$–$C_4$ alkyl radical and a halogen atom chosen from chlorine, bromine, iodine and fluorine,
$R_{23}$ denotes a $C_1$–$C_4$ alkyl radical or a phenyl radical,
$R_{24}$ and $R_{25}$, which may be identical or different, denote a $C_1$–$C_4$ alkyl radical or a phenyl radical or, in the case of structure $G_1$, can together form a benzene ring having at least one substituent chosen from a $C_1$–$C_4$ alkyl radical, a $C_1$–$C_4$ alkoxy radical and an —$NO_2$ radical, and in the case of structure $G_2$, can together form a benzene ring optionally having at least one substituent chosen from a $C_1$–$C_4$ alkyl radical, a $C_1$–$C_4$ alkoxy radical and an —$NO_2$ radical, wherein $R_{24}$ can also denote a hydrogen atom,
Z denotes chosen from an oxygen atom, a sulphur atom or an —$NR_{23}$ radical;
M denotes a —CH radical, a —CR radical wherein R is chosen from a $C_1$–$C_4$ alkyl radical, or an —$NR_{26}(X^-)_r$ radical, wherein r is zero or 1,
K denotes a —CH radical, a —CR radical wherein R is chosen from a $C_1$–$C_4$ alkyl radical, or an —$NR_{26}(X^-)_r$ radical wherein r is zero or 1,
P denotes a —CH radical, a —CR radical wherein R is chosen from a $C_1$–$C_4$ alkyl radical, or an —$NR_{26}(X^-)_r$ radical wherein r is zero or 1,
$R_{26}$ denotes an oxygen atom, a $C_1$–$C_4$ alkoxy radical or a $C_1$–$C_4$ alkyl radical,
$R_{27}$ and $R_{28}$, which may be identical or different, denote a hydrogen atom, a halogen atom chosen from chlorine, bromine, iodine and fluorine, a $C_1$–$C_4$ alkyl radical, a $C_1$–$C_4$ alkoxy radical or an —$NO_2$ radical,
$X^-$ denotes an anion chosen from chloride, iodide, methyl sulphate, ethyl sulphate, acetate and perchlorate, and wherein at least one of K, M or P denotes —$NR_{26}(X^-)_r$, wherein the symbol J is chosen from:

(a) a group of structure $J_1$:

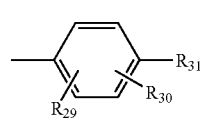
$J_1$ in which,
$R_{29}$ denotes a hydrogen atom, a-halogen atom chosen from chlorine, bromine, iodine and fluorine, a $C_1$–$C_4$ alkyl radical, a $C_1$–$C_4$ alkoxy radical, a —OH radical, an —$NO_2$ radical, an —$NHR_{32}$ radical, an —$NR_{33}R_{34}$ radicals, an —$NHCO(C_1$–$C_4)$alkyl radical, or forms with $R_{30}$ a 5- or 6-membered ring which may contain at least one hetero atom chosen from nitrogen, oxygen and sulphur,
$R_{30}$ denotes a hydrogen atom, a halogen atom chosen from chlorine, bromine, iodine and fluorine, a $C_1$–$C_4$ alkyl radical, a $C_1$–$C_4$ alkoxy radical, or forms, with $R_{31}$ or $R_{32}$ a 5- or 6-membered ring which may contain at least one hetero atom chosen from nitrogen, oxygen and sulphur,
$R_{31}$ denotes a hydrogen atom, an —OH radical, an —$NHR_{32}$ radical or an —$NHR_{33}R_{34}$ radical,
$R_{32}$ denotes a hydrogen atom, a $C_1$–$C_4$ alkyl radical, a $C_1$–$C_4$ monohydroxyalkyl radical, a $C_2$–$C_4$ polyhydroxyalkyl radical or a phenyl radical,
$R_{33}$ and $R_{34}$, which may be identical or different, denote a $C_1$–$C_4$ alkyl radical, a $C_1$–$C_4$ monohydroxyalkyl radical or a $C_2$–$C_4$ polyhydroxyalkyl radical, and (b) a 5- or 6-membered nitrogenous heterocyclic group which can contain at least one other hetero atom and/or at least one carbonyl group and which can have at least one substituent chosen from a $C_1$–$C_4$ alkyl radical, an amino radical or a phenyl radical.

3. A composition according to claim 2, wherein said 5- or 6-membered nitrogenous heterocyclic group is chosen from a group of structure $J_2$:

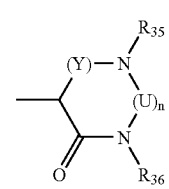
$J_2$ in which,
$R_{35}$ and $R_{36}$, which may be identical or different, denote a hydrogen atom, a $C_1$–$C_4$ alkyl radical, or a phenyl radical, Y denotes a —CO— radical or a radical

wherein n=0 or 1, where, when n denotes 1, U denotes a —CO— radical.

4. A composition comprising, in a cosmetically acceptable support suitable for dyeing the hair, at least one direct dye and at least one crosslinked polymer containing acrylic residue units of the structure

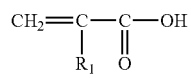

in which $R_1$ denotes H, $CH_3$ or $C_2H_5$, and $C_{10}$–$C_{30}$ alkyl acrylate residue units, wherein said composition is a direct dyeing composition for the hair, wherein said at least one direct dye is a cationic anthraquinonic dye of formula (IX):

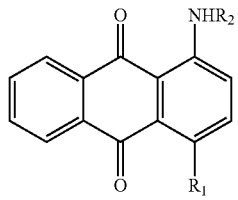

in which:

$R_1$ denotes a hydrogen atom, a —OH radical, a —$NH_2$ radical, or a —NH($C_1$–$C_4$)alkyl radical, $R_2$ denotes a —$(CH_2)_n NR_3 R_4 (R_5)_m$— radical, in which n denotes 1 or 10, m denotes zero or 1, and $R_3$, $R_4$, $R_5$ which may be identical or different, denotes a hydrogen atom or a $C_1$–$C_4$ alkyl radical, and wherein $R_3$ and $R_4$, with the nitrogenous atom, can form a 5- or 6-membered heterocycle group which can contain at least one other hetero atom chosen from nitrogen, oxygen or sulphur and optionally having at least one substituent chosen from $C_1$–$C_4$ alkyl radicals, amino radicals, and phenyl radicals.

* * * * *

UNITED STATES PATENT AND TRADEMARK OFFICE
CERTIFICATE OF CORRECTION

PATENT NO. : 7,056,346 B1
APPLICATION NO. : 09/663942
DATED : June 6, 2006
INVENTOR(S) : Mireille Maubru It is certified that error appears in the above-identified patent and that said Letters Patent is hereby corrected as shown below:

In claim 1, column 19, lines 60-63,

" 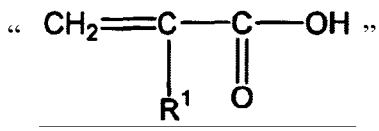 "

should read

-- 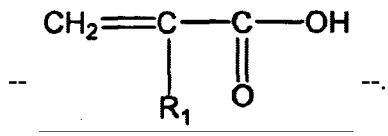 --.

In claim 2, column 23, line 46, "$A_{13}$" should read --$A_{16}$--.

In claim 2, column 23, line 52, "$A_{14}$" should read --$A_{17}$--.

In claim 2, column 23, line 57, "$A_{15}$" should read --$A_{18}$--.

In claim 2, column 24, line 12, "R8" should read --$R_8$--.

In claim 2, column 24, line 14, "R9" should read --$R_9$--.

In claim 2, column 24, line 28, "$R^{11}$" should read --$R_{11}$--.

In claim 2, column 25, line 5, "et" should read --and--.

In claim 2, column 27, line 51, "denotes chosen from an" should read --denotes an--.

In claim 2, column 28, line 20, "a-halogen" should read --a halogen--.

In claim 2, column 28, line 24, "radicals," should read --radical,--.

UNITED STATES PATENT AND TRADEMARK OFFICE
CERTIFICATE OF CORRECTION

PATENT NO. : 7,056,346 B1
APPLICATION NO. : 09/663942
DATED : June 6, 2006
INVENTOR(S) : Mireille Maubru It is certified that error appears in the above-identified patent and that said Letters Patent is hereby corrected as shown below:

In claim 4, column 30, line 19, "$R_3$, $R_4$, $R_5$ which may be identical or different, denotes a" should read --$R_3$, $R_4$, and $R_5$, which may be identical or different, denote a--.

Signed and Sealed this

Tenth Day of October, 2006

JON W. DUDAS
*Director of the United States Patent and Trademark Office*